US007646850B2

(12) United States Patent  (10) Patent No.: US 7,646,850 B2
MacDonald  (45) Date of Patent: Jan. 12, 2010

(54) WIDE-FIELD, COHERENT SCATTER IMAGING FOR RADIOGRAPHY USING A DIVERGENT BEAM

(75) Inventor: Carolyn A MacDonald, Duanesburg, NY (US)

(73) Assignee: The Research Foundation of State University of New York, Albany, NY (US)

( * ) Notice: Subject to any disclaimer, the term of this patent is extended or adjusted under 35 U.S.C. 154(b) by 187 days.

(21) Appl. No.: 11/624,437

(22) Filed: Jan. 18, 2007

(65) Prior Publication Data

US 2008/0175350 A1 Jul. 24, 2008

(51) Int. Cl.
*G01N 23/201* (2006.01)
*G01N 23/20* (2006.01)
(52) U.S. Cl. .......................... 378/87; 378/86
(58) Field of Classification Search ............... 378/7, 378/37, 70, 86–90, 154, 156, 157
See application file for complete search history.

(56) References Cited

U.S. PATENT DOCUMENTS

| 4,948,974 | A |   | 8/1990  | Nelson et al. ............ 250/358.1 |
|-----------|---|---|---------|-------------------------------------|
| 5,394,454 | A | * | 2/1995  | Harding ........................ 378/86 |
| 5,805,662 | A |   | 9/1998  | Kurbatov et al. ............... 378/87 |
| 5,987,095 | A |   | 11/1999 | Chapman et al. ............... 378/70 |
| 6,005,913 | A |   | 12/1999 | Zombo et al. .................. 378/71 |
| 6,442,233 | B1| * | 8/2002  | Grodzins et al. ............... 378/57 |
| 6,483,891 | B1|   | 11/2002 | Lazarev et al. ................ 378/37 |
| 6,625,253 | B1| * | 9/2003  | Barnes et al. ................ 378/155 |
| 6,947,521 | B2|   | 9/2005  | Wernick et al. ................ 378/70 |
| 2005/0094767 | A1| * | 5/2005  | Francke et al. ................ 378/87 |
| 2005/0243970 | A1| * | 11/2005 | Bernhardt ..................... 378/156 |
| 2007/0253532 | A1| * | 11/2007 | Van Stevendaal et al. ..... 378/87 |
| 2008/0118033 | A1| * | 5/2008  | Klausz ........................ 378/154 |
| 2008/0240342 | A1| * | 10/2008 | Thran et al. ................... 378/19 |

(Continued)

FOREIGN PATENT DOCUMENTS

WO   WO 2005120354 A1 * 12/2005

OTHER PUBLICATIONS

Batchelar et al., "Material-Specific Analysis Using Coherent-Scatter Imaging," Medical Physics vol. 29 No. 8, Aug. 2002, pp. 1651-1660.

(Continued)

*Primary Examiner*—Edward J Glick
*Assistant Examiner*—Anastasia Midkiff
(74) *Attorney, Agent, or Firm*—Kevin P. Radigan, Esq.; Heslin Rothenberg Farley & Mesiti P.C.

(57) ABSTRACT

The present invention provides a method and system for detecting a material in an object to be analyzed in a radiographic imaging system. The method includes providing wide-field illumination of an object with partially monochromatic x-ray radiation from a divergent source without restrictively collimating the x-ray radiation. The x-ray radiation scattered by the object outside of a predetermined range of angles defined about a characteristic angle is rejected. The characteristic angle is a scattering angle about which a material of the object coherently scatters the incident x-ray radiation. In addition, the method includes the step of detecting coherently-scattered radiation, which is the x-ray radiation diffracted by the object within the predetermined range of angles defined about the characteristic angle.

20 Claims, 10 Drawing Sheets

U.S. PATENT DOCUMENTS

2009/0060124 A1\* 3/2009 Grass et al. ............... 378/19
2009/0074132 A1\* 3/2009 Schlomka et al. ........... 378/19

OTHER PUBLICATIONS

Bradley, et al., "Quantitative Measurement of Small-Angle Gamma Ray Scattering From Water, Nylon, and Lucite," Medical Physics vol. 16 No. 6, Nov./Dec. 1989, pp. 851-857.

Harding et al., "X-ray Diffraction Computed Tomograph," Medical Physics vol. 14 No. 4, Jul./Aug. 1987, pp. 515-525.

Kidane et al., "X-ray Scatter Signatures for Normal and Neoplastic Breast Tissues," Phys. Med. Biol. 44 (1999) pp. 1791-1802.

Kosanetzky et al., "X-ray Diffraction Measurements of Some Plastic Materials and Body Tissues," Medical Physics vol. 14 No. 4, Jul./Aug. 1987, pp. 526-532.

Leclair, et al., "A Semianalytic Model to Investigate the Potential Applications of X-ray Scatter Imaging," Medical Physics vol. 25 No. 6, Jun. 1998, pp. 1008-1020.

Westmore, et al., "Angular-Dependent Coherent Scatter Measured with a Diagnostic X-ray Image Intensifier-Based Imaging System," Medical Physics vol. 23 No. 5, May 1996, pp. 723-733.

\* cited by examiner

WIDE-FIELD, COHERENT SCATTER IMAGING FOR RADIOGRAPHY USING A DIVERGENT BEAM

GOVERNMENT RIGHTS STATEMENT

This invention was made with U.S. Government support under Grant No. DAMD17-02-1-0517 from the Department of Defense Breast Cancer Research Program. The U.S. Government has certain rights in the invention.

BACKGROUND OF THE INVENTION

1. Technical Field

The present invention generally relates to radiography. More particularly, the present invention relates to coherent-scatter imaging for radiography using a divergent beam over a wide field of an object to be analyzed.

2. Background Information

Mammography is the primary screening tool for the detection of breast cancer. Improved specificity is desirable because false positives may cause the patient unnecessary trauma and lead to unnecessary biopsies and because false negatives may cause delayed treatment.

Contrast in conventional mammography systems is created when x-rays are removed by absorption and by scattering, which redirects the paths of incident x-ray beams. In conventional radiography systems, a grid of lead ribbons is placed between the patient and x-ray detector to remove the scattered x-rays from the resulting image.

However, it is known that different tissue types characteristically produce coherent scatter at small diffraction angles. If a small tissue sample is irradiated with a pencil beam (i.e., a highly collimated beam) of x-rays, a narrow cone of coherent scatter is produced around the primary beam that is transmitted by the sample. Therefore, it may be possible to obtain additional information about tissue type present in the sample by measuring the cone angle of the coherently diffracted x-ray radiation. Because a highly-collimated pencil beam only illuminates a small area of a subject to be analyzed, the pencil beam must be scanned over an entire area of a subject in order to obtain an image of the entire subject. This presents two problems. One is the time required to completely scan the subject. Thus, a need exists for a radiographic system that reduces the time required to obtain an image of a subject to be analyzed. The second problem is that conventional radiographic systems illuminate a patient with a wide field of x-ray radiation rather than a pencil beam. Therefore, a need exists for a method of detecting coherently-scattered radiation that is compatible with existing wide-field radiographic systems.

SUMMARY OF THE INVENTION

Briefly, the present invention provides a method and system for detecting a material in an object to be analyzed in a radiographic imaging system. In one aspect, the method comprises providing wide-field illumination of an object with partially monochromatic x-ray radiation from a divergent source without restrictively collimating the x-ray radiation. The method also comprises rejecting the x-ray radiation scattered by the object outside of a predetermined range of angles defined about a characteristic angle, wherein the characteristic angle is a scattering angle about which a material of the object coherently scatters the incident x-ray radiation. In addition, the method includes detecting coherently-scattered radiation, which comprises the x-ray radiation diffracted by the object within the predetermined range of angles defined about the characteristic angle. In accordance with various embodiments of the present invention, the entire object to be analyzed or a wide-field portion of the object may be illuminated by the source at once.

In accordance with another embodiment of the present invention, the method further comprises rejecting the x-ray radiation scattered at angles greater than a predetermined angle by the object to be analyzed and detecting transmitted radiation, which comprises the x-ray radiation passing through the object and not scattered by the object at angles greater than the predetermined angle. In one exemplary embodiment, existing wide-beam radiography systems may be retrofit in accordance with the method.

These, and other objects, features and advantages of this invention will become apparent from the following detailed description of the various aspects of the invention taken in conjunction with the accompanying drawings.

DETAILED DESCRIPTION OF THE INVENTION

A method and system for detecting a material in an object to be analyzed in a radiographic imaging system, in accordance with the present invention, utilize a divergent source of partially monochromatic x-ray radiation. The divergent source is configured to provide wide-field illumination of the object with the incident x-ray radiation. In accordance with one embodiment of the present invention, the entire object to be analyzed is illuminated by the source at once. In another embodiment, a wide-field portion of the object is illuminated by the source at once. Although wide-field illumination in accordance with the present invention may include a fan beam, for example, the provision of wide-field illumination in accordance with the present invention does not require the use of restrictive collimation. That is, pencil-beam illumination comprising substantially parallel rays is not required. The method and system of the present invention utilize at least one detector that is positioned to detect radiation that is coherently-scattered by the object that is being analyzed. More particularly, at least one detector is positioned to detect radiation that is diffracted within a predetermined range of angles defined about a characteristic angle, about which a material of the object coherently scatters incident radiation. Advantageously, the method and system utilize at least one scatter-rejection means to reject radiation that is scattered outside of the predetermined range of angles defined about the characteristic angle of the material of interest.

Figure 1:
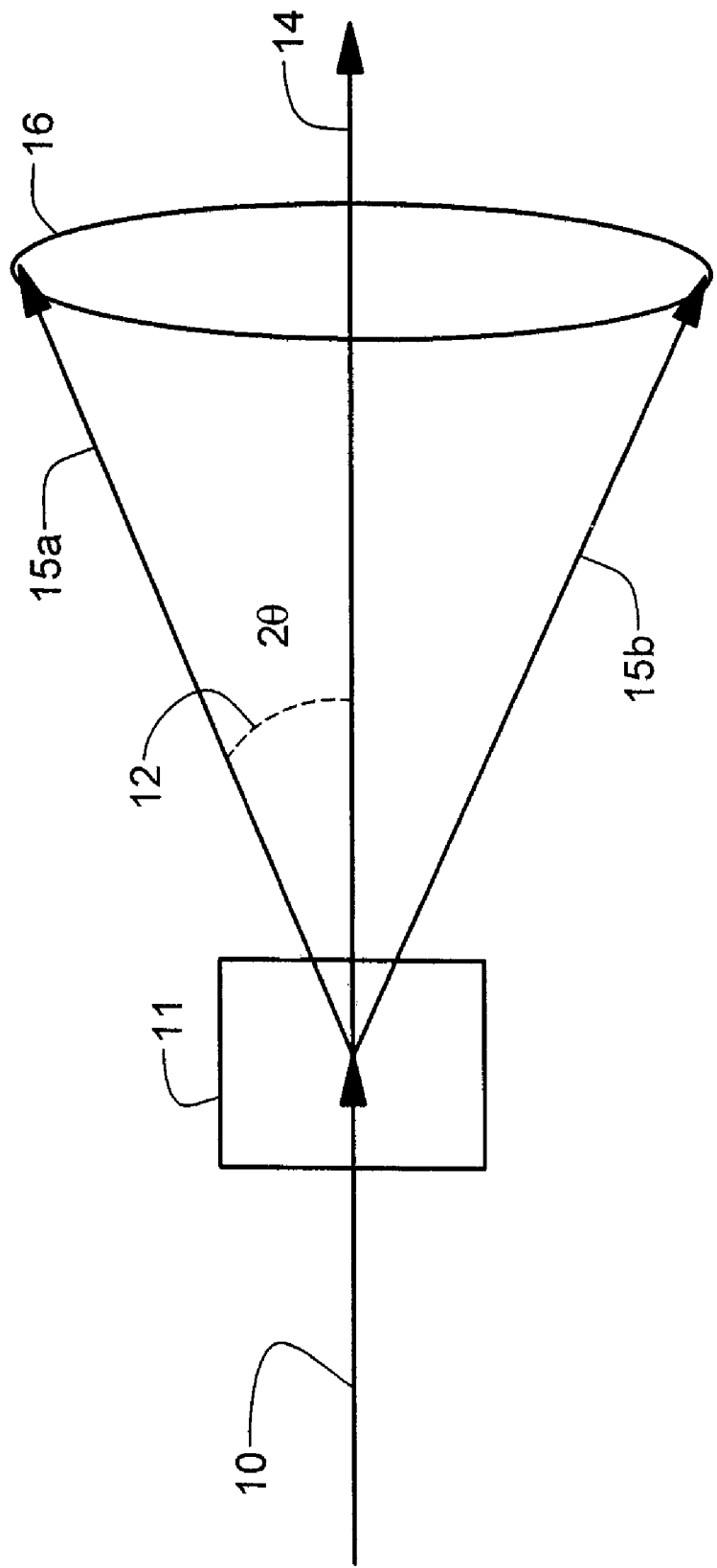
FIG. 1 illustrates the conical pattern of coherently-scattered radiation resulting from diffraction of incident x-ray radiation by a small volume of material in an object.

Bragg's Law characterizes the coherent scatter produced by repetitive structures in a material as $n\lambda = 2d \sin \theta$, where n is an integer, $\lambda$ is the x-ray's wavelength, d is the spacing characteristic of the material's structure, and $\theta$ is one half of the coherent scatter angle, as shown in FIG. 1. The spacing characteristic may be the plane spacing in a crystal, for example, or the fiber spacing in collagen, as another example. As illustrated in FIG. 1, a portion of incident x-ray radiation 10, which illuminates object 11, passes through object 11 as transmitted radiation 14. Object 11 may comprise a material that coherently scatters a portion of incident radiation 10 at characteristic angle 12, denoted $2\theta$ in the equation for Bragg's Law. The coherently scattered radiation from a small volume of the material forms a conical pattern as illustrated in FIG. 1 and comprises coherently-scattered beams 15a and 15b. Consequently, base 16 of this conical pattern of coherently scattered radiation may be detected as an ellipse or ring by a planar detector.

Figure 2:
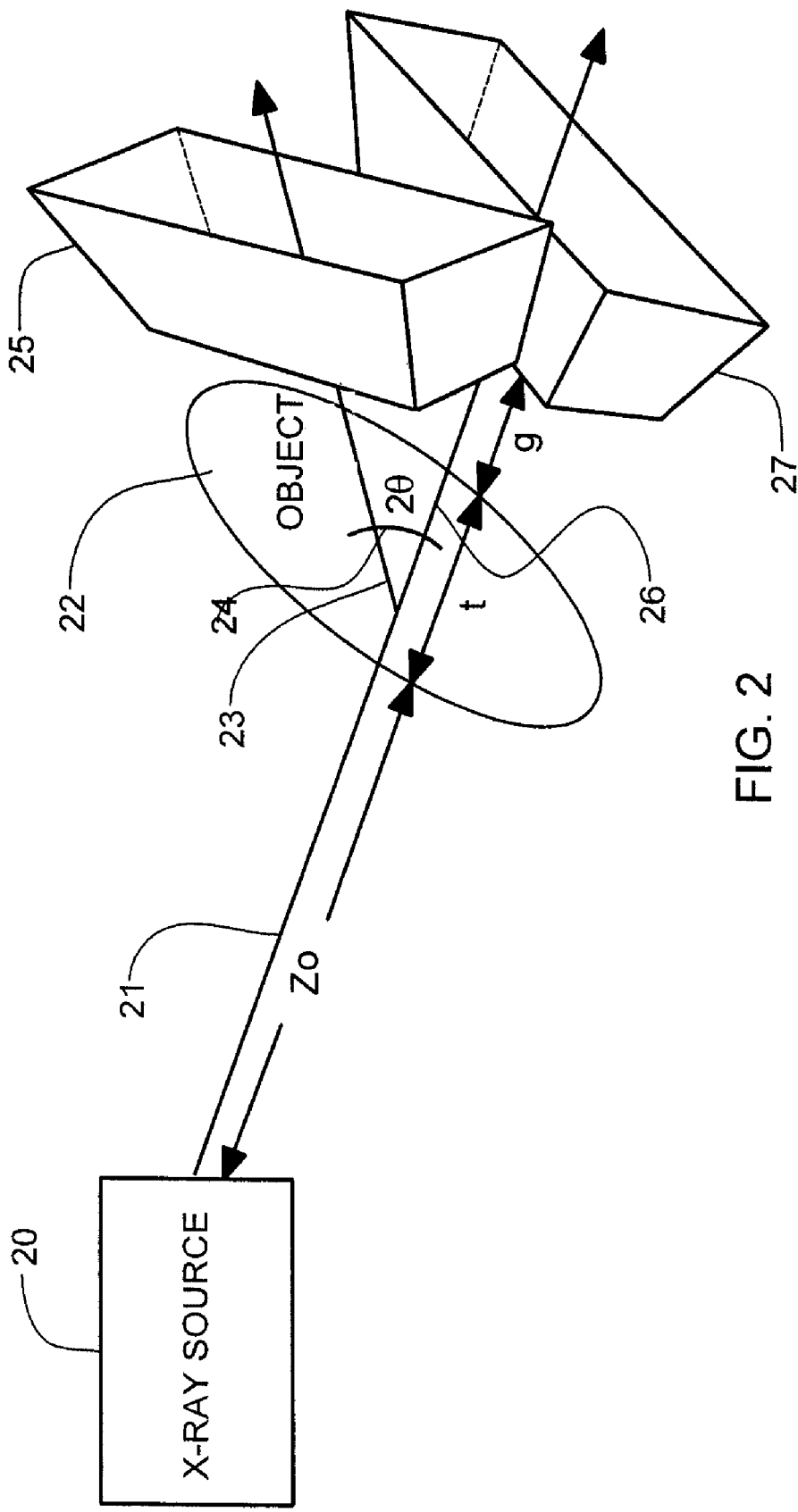
FIG. 2 illustrates one embodiment of a system for selective transmission of radiation that is coherently scattered by an object.

As illustrated in FIG. 2, an angular filter may be used to transmit a section of the conical pattern of coherently-scattered radiation and to block radiation that is scattered at angles outside of a predetermined range of angles about the characteristic angle of a material of interest. FIG. 2 illustrates one embodiment of a system for selective transmission of radiation that is coherently scattered by an object. The system of FIG. 2 comprises x-ray source 20, which illuminates object 22 with incident radiation 21 having a wide-field beam. A portion of the incident x-ray radiation is diffracted or coherently scattered at characteristic angle 24 by a material comprising object 22, resulting in coherently-scattered radiation 23. Grid 25 or other scatter-rejection means transmits radiation that is scattered by object 22 within a predetermined range of angles about the characteristic angle of the material of interest. Advantageously, grid 25 or other scatter-rejection means blocks radiation that is diffusely scattered outside of the predetermined range of angles about the characteristic angle of the material of interest. Optionally, primary-path grid 27 or other primary-path scatter-rejection means may be utilized to facilitate detection of transmitted radiation 26 and rejection of radiation scattered at angles greater than a predetermined angle.

Figure 3:
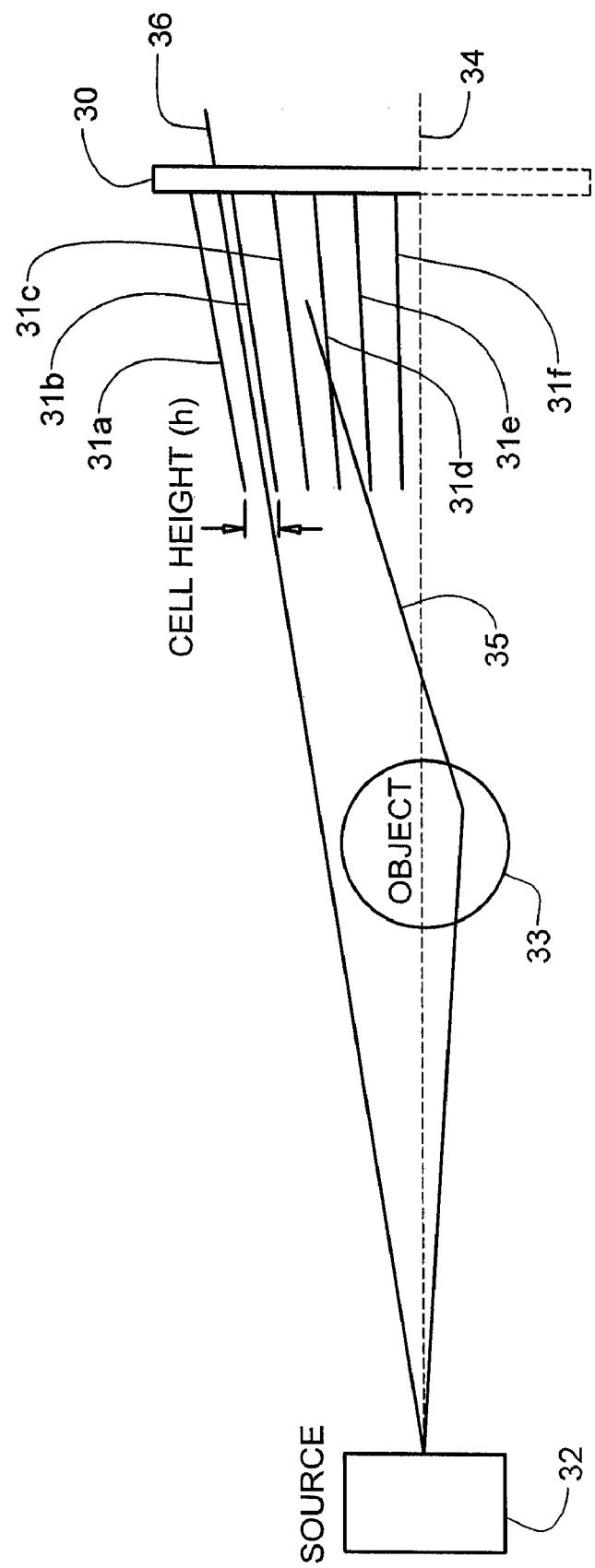
FIG. 3 illustrates a cross-sectional view of one embodiment of a scatter-rejection grid for a radiographic system in accordance with the present invention.

FIG. 3 illustrates a cross-sectional view of one embodiment of a scatter-rejection grid for an x-ray system. In FIG. 3, scatter-rejection grid 30 is positioned to pass primary-path rays that pass through or around an object that is illuminated with a divergent source of x-ray radiation having a wide field and to block rays that are scattered at angles greater than a predetermined angle by the object. In the embodiment illustrated in FIG. 3, scatter-rejection grid 30 comprises a plurality of ribbons 31a, 31b, 31c, 31d, 31e, 31f of a highly x-ray absorbing material, such as lead interspersed with a low Z interspacing material such as carbon fiber. For the linear grid illustrated in FIG. 3, the lead ribbons are arranged to be parallel to the, x-ray beams emitted by the source, and the lead ribbons extend out of the plane of the paper. Also, as illustrated in FIG. 3, lines extending from the ribbon cross-sections intersect at a focal point of the grid. A grid's focal point is typically located at a system's x-ray source. Scatter-rejection grid 30 transmits primary beam 34 from divergent source 32 that passes through object 33 and primary beam 36 from divergent source 32 that bypasses object 33, while scatter-rejection grid 30 blocks scattered ray 35, which is scattered by object 33 at an angle greater than a predetermined angle. Scatter-rejection grid 30 may be characterized by its grid ratio, which is the ratio of the grid's width (i.e., the length of the cross-section of ribbons 31 illustrated in FIG. 3) to the spacing between adjacent ribbons.

In another embodiment, a scatter-rejection means may comprise a two-dimensional, crossed grid of ribbons. In this embodiment, ribbons 31a-31f are intersected by additional ribbons that are also parallel to the beams emitted by source 32, but perpendicular to ribbons 31a-31f. Other embodiments of scatter-rejection means include soller slits and polycapillary optic angular filters.

Figure 4:
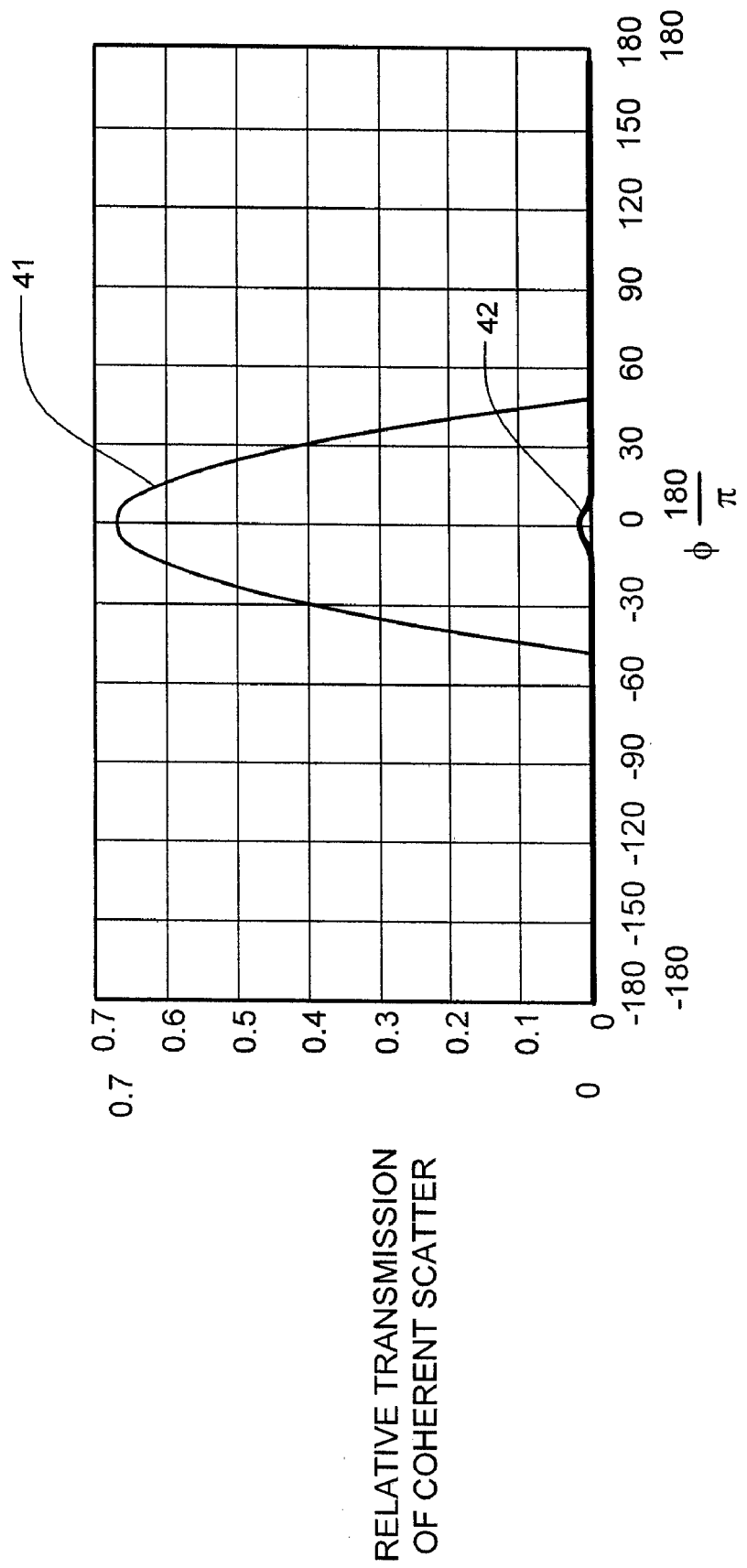
FIG. 4 illustrates the relative transmission of coherent scatter as a function of out of plane angle $\phi$ for malignant tissue scattering at a characteristic angle of 13 degrees and fat scattering at a characteristic angle of 9 degrees, where the scatter-rejection grid is aligned at 15 degrees relative to the primary x-ray beam.
Figure 5:
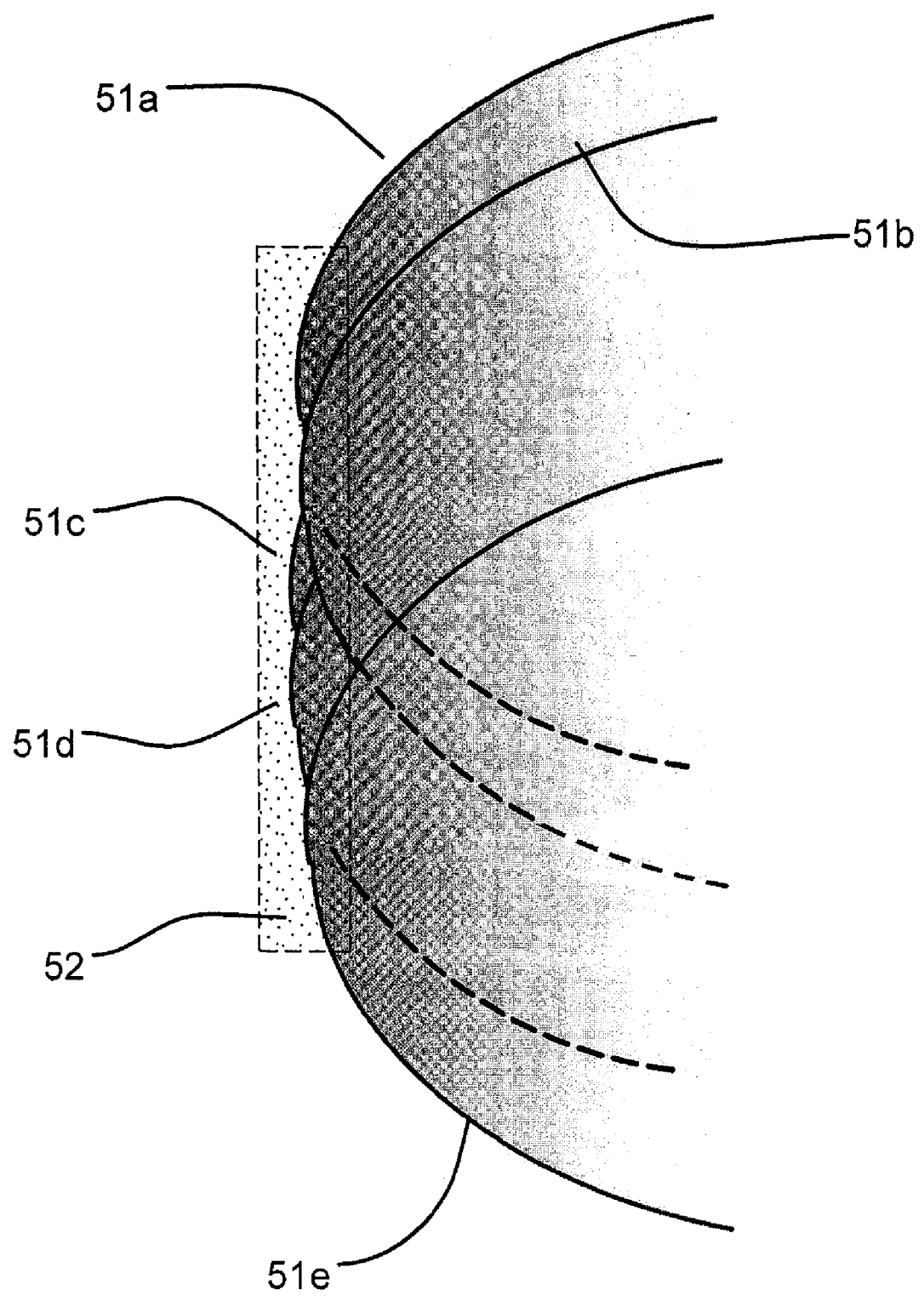
FIG. 5 illustrates an example of a map formed by overlapping sections of coherent scatter rings from different locations in an object to be analyzed, wherein the map indicates the location of a type of tissue in a patient.

In accordance with an aspect of the present invention, an angular filter or scatter-rejection grid is employed to transmit a section of one or more cones of coherently-scattered radiation that is diffracted by an object illuminated by x-ray radiation. The radiation transmitted by the scatter-rejection grid may be detected by an x-ray detector to produce an intensity signal for the radiation scattered at a characteristic angle or to image a map of the locations in the object from which the scatter cones originate. Advantageously, with this technique, a large area of an object to be tested may be illuminated at one time. The use of a scatter-rejection grid to facilitate the detection of coherent scatter is illustrated in FIG. 2. Only part of the circular ring defining the base of the conical pattern of coherently scattered radiation passes through the scatter-rejection grid, as illustrated in the plot in FIG. 4, for example, which shows the relative transmission of coherent scatter as a function of out of plane angle $\phi$ for malignant tissue scattering at a characteristic angle of 13 degrees and fat scattering at a characteristic angle of 9 degrees, where the scatter-rejection grid is aligned at 15 degrees relative to the primary beam transmitted through the subject and has a grid ratio of 10:1. In FIG. 4, plot 41 illustrates the relative transmission of coherent scatter from malignant tissue, and plot 42 illustrates the relative transmission of coherent scatter from fatty tissue. The partial rings of coherently-scattered radiation passing through the grid form overlapping partial ellipses on the imaging detector, as illustrated in FIG. 5. Several resulting overlapping partial ellipses 51a-51e are shown in FIG. 5 by way of example. In FIG. 5, overlap of the sections of coherent scatter rings from different locations in the object form a map, for example, of the tissue locations in the patient. In this example, the overlapped sections form an image 52 of a rectangular region in the object that coherently scatters the incident radiation.

Figure 6:
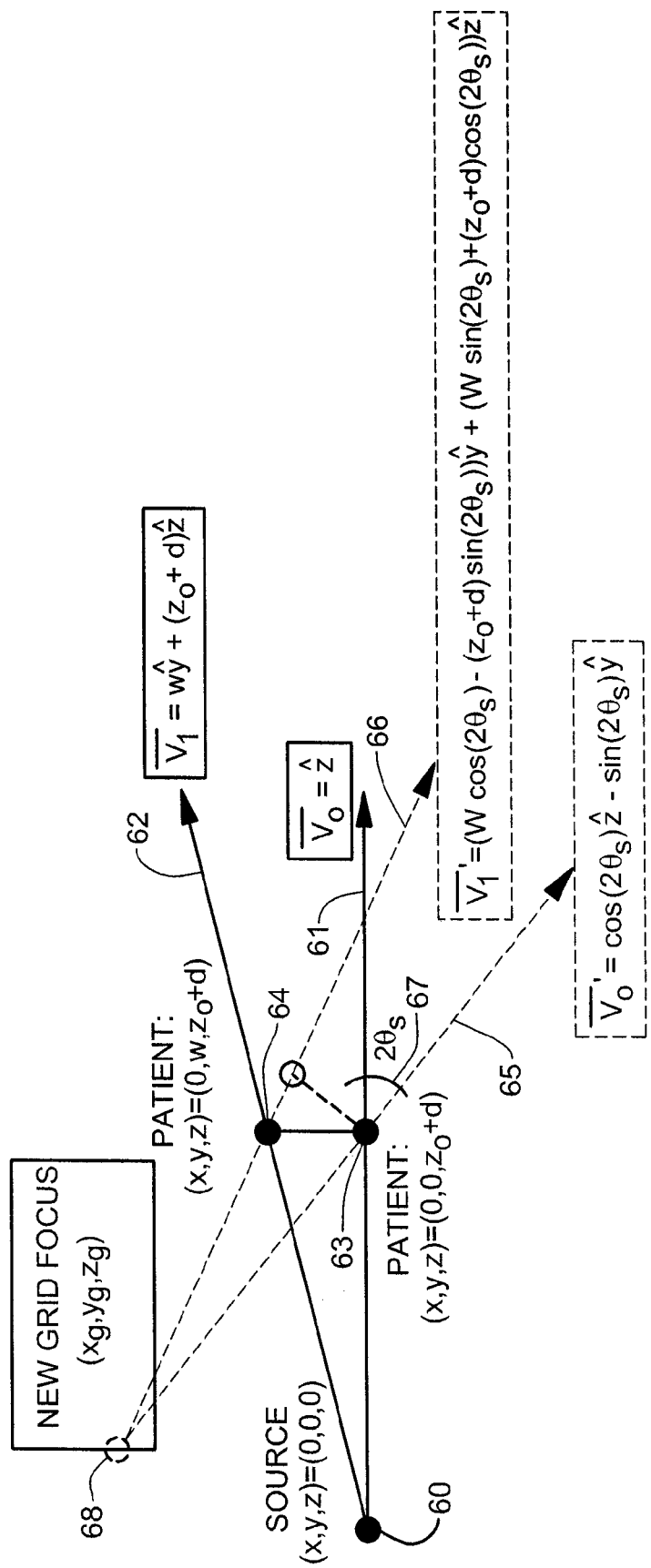
FIG. 6 illustrates the geometry of coherent scatter and grid alignment for detecting coherent scatter from a material of interest.

FIG. 6 illustrates the geometry of coherent scatter and grid alignment for detecting coherent scatter of interest. Primary x-ray beams 61 and 62 emanate from source 60 such that primary beam 61 passes through point 63 of an object to be analyzed and primary beam 62 passes through point 64 of the object. The directions of the coherent scatter from points 63 and 64 are illustrated by scattered beam 65 and scattered beam 66, respectively. Scattered beams 65 and 66 are diffracted at coherent-scattering angle 67 ($2\theta_s$) by the object to be analyzed. As shown in FIG. 6, the grid focal point is located at the intersection of the dashed lines representing the directions of scattered beam 65 through point 63, having coordinates (0,0,$z_o$+d), and scattered beam 66 through point 64, having coordinates (0,w, $z_o$+d). Therefore, the coordinates ($x_g$, $y_g$, $z_g$) of the grid focal point 68 may be obtained by solving the following equation:

$$\begin{pmatrix} 0 \\ 0 \\ z_o + d \end{pmatrix} + \alpha \begin{pmatrix} 0 \\ -\sin(2\theta_s) \\ \cos(2\theta_s) \end{pmatrix} = \begin{pmatrix} 0 \\ w \\ z_o + d \end{pmatrix} + \beta \begin{pmatrix} 0 \\ w\cos(2\theta_s) - (z_o + d)\sin(2\theta_s) \\ w\sin(2\theta_s) + (z_o + d)\cos(2\theta_s) \end{pmatrix}$$

$$\Rightarrow \beta = -\cos(2\theta_s), \quad \alpha = -w\sin(2\theta_s) - (z_o + d)\cos(2\theta_s)$$

$$\Rightarrow \begin{pmatrix} x_g \\ y_g \\ z_g \end{pmatrix} = \begin{pmatrix} 0 \\ w\sin^2(2\theta_s) + (z_o + d)\cos(2\theta_s)\sin(2\theta_2) \\ -w\cos(2\theta_s)\sin(2\theta_s) + (z_o + d)\sin^2(2\theta_s) \end{pmatrix}$$

As illustrated in FIG. 6, x-ray source 60 is a distance $z_o$ from the patient, and d is the depth of a selected point in the patient; typically d is chosen to be approximately t/2, where t is the patient thickness. Referring to FIGS. 2 and 6, it is apparent that the focal length of the grid is then f=$z_o$+d+g, where g is the distance between the patient and the grid. The choice of w, $z_o$, and g affect the optimization of the discrimination between different tissue types.

Figure 7A:
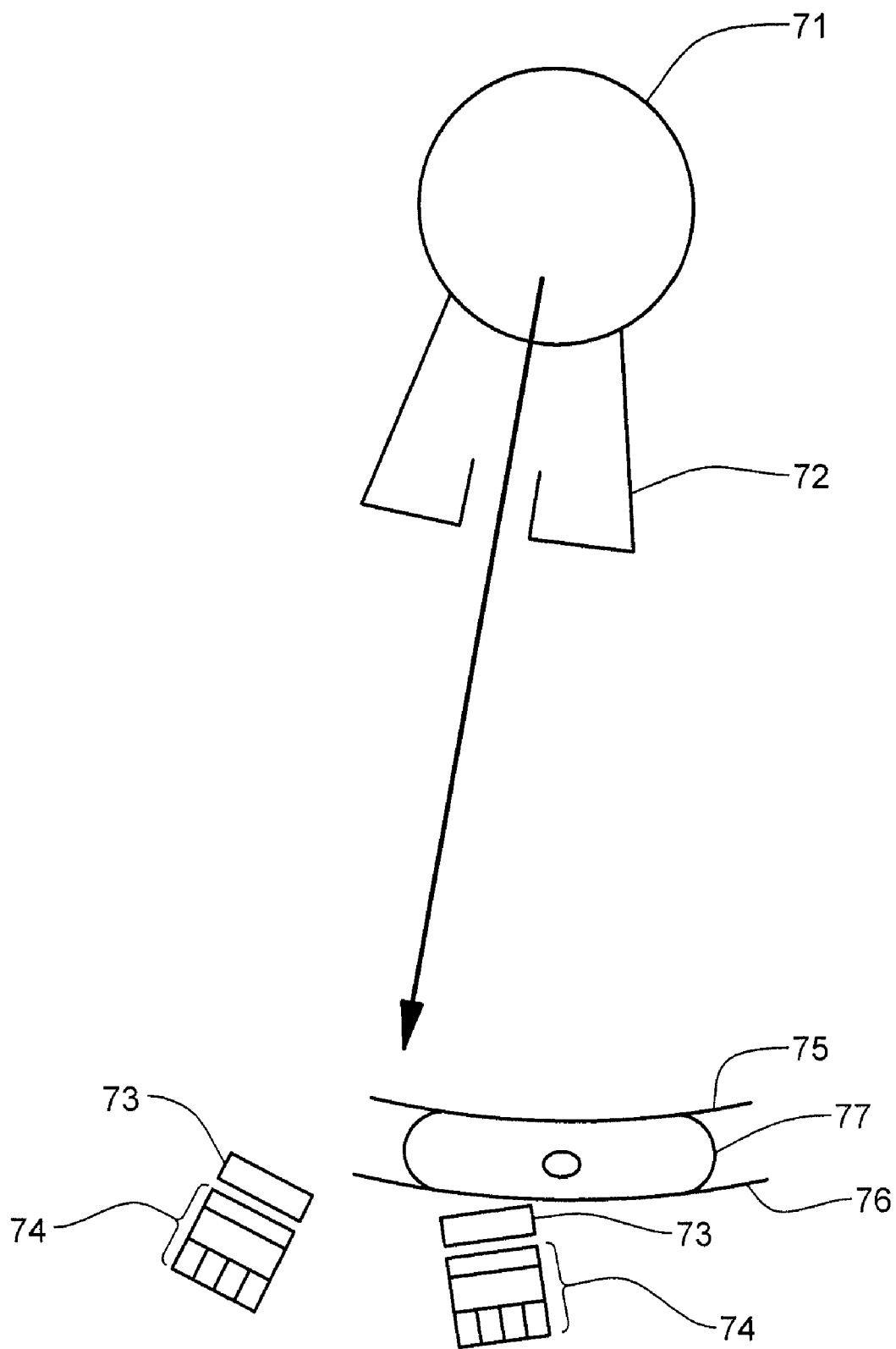
FIG. 7A illustrates a front view of one embodiment of a mammography system in accordance with the present invention.
Figure 7B:
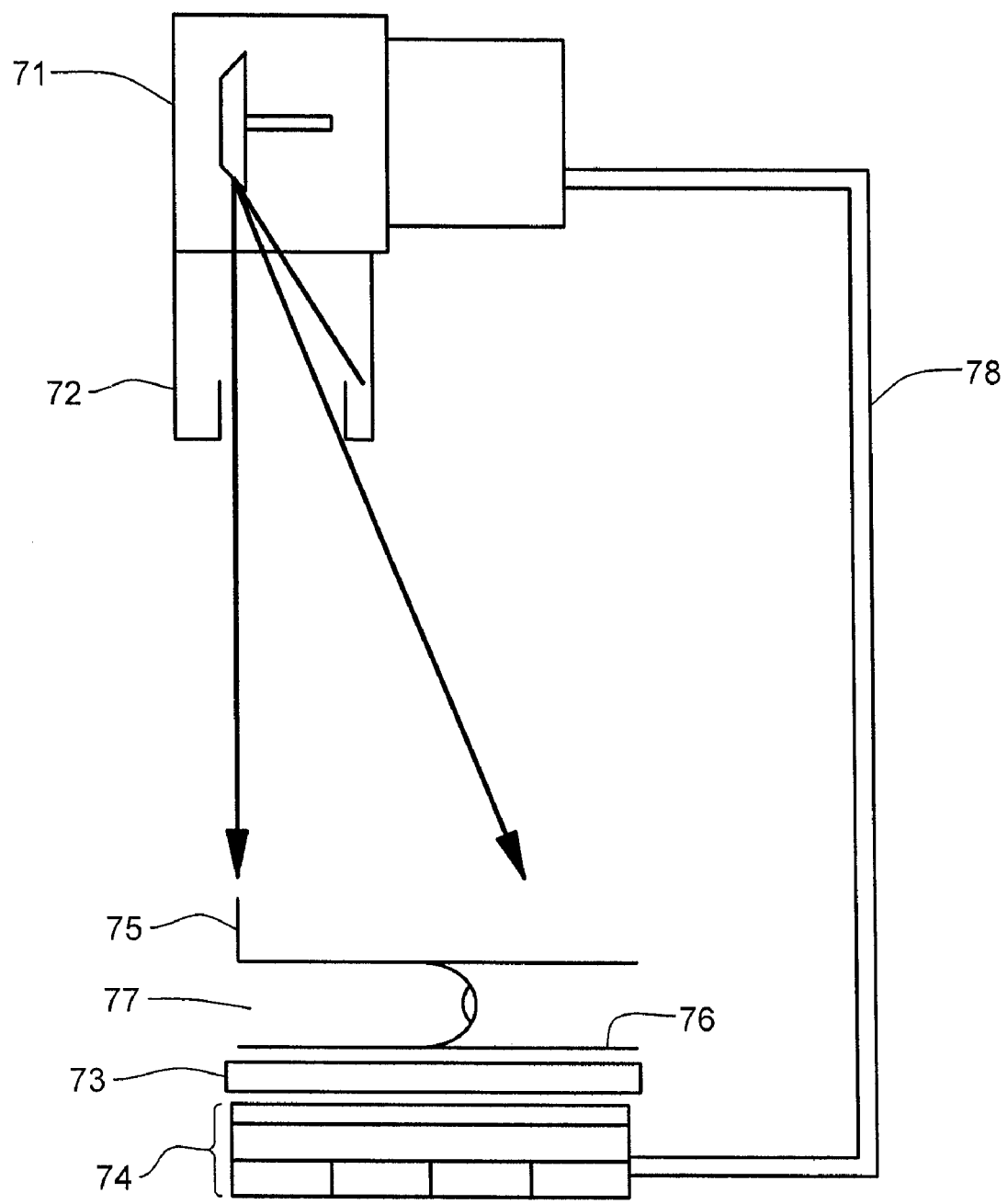
FIG. 7B illustrates a side view of the embodiment of a mammography system shown in FIG. 7A.

One embodiment of a radiographic imaging system for detecting a material in an object to be analyzed, in accordance with the present invention, is illustrated in FIGS. 7A and 7B. This embodiment comprises x-ray source 71, slot 72 for producing a fan beam from the x-ray radiation emitted by x-ray source 71, grids 73, and x-ray detectors 74 for detecting coherently scattered radiation that is diffracted by a material of interest. Grids 73 are positioned to reject x-ray radiation that is scattered by an object to be analyzed outside of a predetermined range of angles that are defined about a characteristic angle of the material of interest. The characteristic angle of a material is a scattering angle about which the material of the object coherently scatters incident x-ray radiation. X-ray detectors 74 are positioned to detect the coherently scattered radiation that passes through grids 73.

In the example of FIG. 7A, the object to be analyzed is a breast 77. The mammography system in this example may also comprise compression paddle 75 and table top 76. As indicated in the front view of FIG. 7A, the x-ray fan beam source, comprising x-ray source 71 and slot 72 rotates to facilitate scanning the object with a fan beam of x-ray radiation. Grids 73 and x-ray detectors 74 rotate together with the x-ray fan beam source to facilitate analyzing the entire object by detecting the radiation coherently scattered by the object as the scan proceeds across the object. In the example of FIG. 7A, detectors 74 comprise a CsI phosphor layer, a fiber optic taper, and a charge coupled device (CCD).

FIG. 7B illustrates a side view of this embodiment of a radiographic imaging system for detecting a material in an object to be analyzed. The side view of FIG. 7B illustrates swing arm 78 for facilitating the coordinated rotation of the x-ray fan beam source, grids 73, and x-ray detectors 74.

Figure 8:
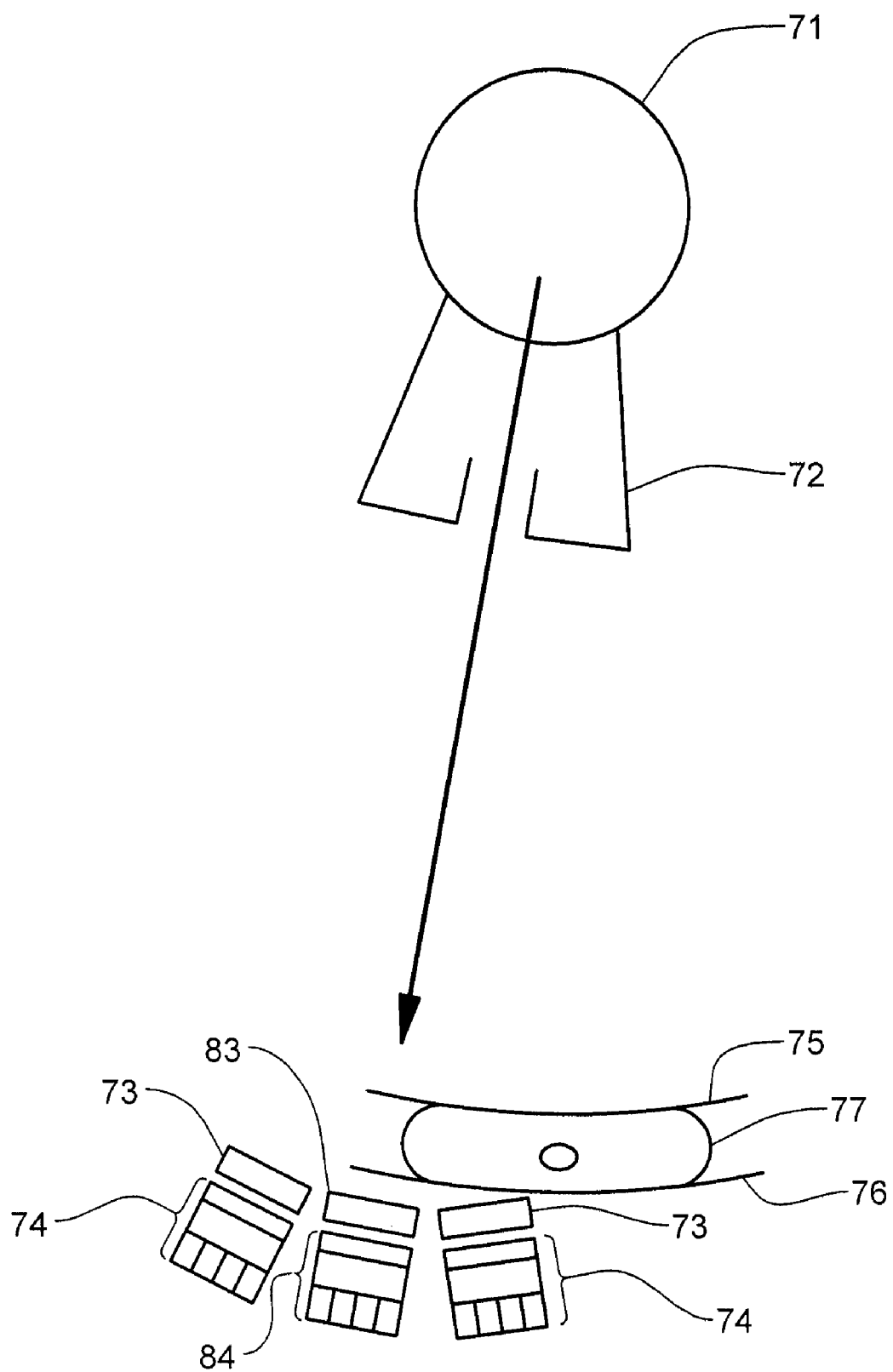
FIG. 8 illustrates a front view of another embodiment of a radiographic imaging system for detecting a material in an object to be analyzed, in accordance with the present invention.

FIG. 8 illustrates a front view of another embodiment of a radiographic imaging system for detecting a material in an object to be analyzed, in accordance with the present invention. In the embodiment of FIG. 8, the system comprises x-ray source 71, slot 72 for producing a fan beam from the x-ray radiation emitted by x-ray source 71, grids 73, and x-ray detectors 74 for detecting coherently scattered radiation that is diffracted by a material of interest. Grids 73 are positioned to reject x-ray radiation that is scattered by an object to be analyzed outside of a predetermined range of angles that are defined about a characteristic angle of the material of interest. X-ray detectors 74 are positioned to detect the coherently scattered radiation that passes through grids 73. In addition, this embodiment of the system also comprises grid 83 for rejecting x-ray radiation scattered by the object to be analyzed at angles greater than a predetermined angle and detector 84 for detecting transmitted x-ray radiation, which passes through the object to be analyzed and grid 83.

The method of the present invention may produce a signal indicative of the presence of a particular tissue type or other structure, organic or inorganic, with or without an image mapping the location of the structure using coherent scatter (also known as powder diffraction) in a system that samples a wide field of an object in a single shot. In one embodiment, the method provides tissue or other material detection with concurrent radiographic imaging. FIGS. 7A, 7B, and 8 illustrate examples of embodiments of systems comprising a conventional slot scan mammography imaging system that provide wide-field tissue typing, in accordance with the present invention.

The following provides an additional description of the x-ray fan beam source in FIGS. 7A, 7B, and 8. X-ray source 71 that emits x-ray radiation may be an x-ray tube, for example. Slot 72 shapes the x-ray radiation emitted by x-ray source 71 to produce a fan beam. The fan beam is then rotated about the x-ray tube's focal spot to scan across the object to be analyzed. The x-ray detector assembly comprises a narrow strip which rotationally translates together with the fan beam. For mammography, the x-ray tube typically has a Mo or Ag anode and is operated at 20-35 kV. A transmission filter may be used to suppress low energy radiation. For general radiography, a W anode may be employed with higher tube voltage. For industrial radiography of thinner objects, Cu anodes may be employed.

To facilitate analysis of coherent scatter, a quasi-monochromatic or partially monochromatic beam is utilized. A partially monochromatic beam may be obtained from a transmission filter having an absorption edge between the $\alpha$ and $\beta$ characteristic lines of the x-ray source. For example, a Zr filter may be used with a Mo source; a Rh filter may be used with an Ag source; or a Ni filter may be used with a Cu source. An additional filter may be used to suppress bremsstrahlung high-energy radiation. For example, a Mo or Rh filter may be used to filter x-ray radiation from a Mo source to suppress bremsstrahlung radiation. Alternatively, a monochromator such as a graphite crystal may be used. To increase the intensity after the monochromator, the monochromator may be curved, or may be employed with a collimating optic such as a polycapillary optic between the source and the monochromator crystal. The use of a monochromator may improve the selectivity of detection of coherently scattered radiation and reduce the background noise.

In some embodiments, such as those illustrated in FIGS. 7A, 7B, and 8 for example, a scatter rejection device may be inserted between an object to be analyzed and the x-ray detector. For analyzing thick objects, as in medical radiography, the detector assembly may be preceded by a scatter rejection device to reduce the background fog from Compton scattering. This scatter rejection device may be a simple air gap if the patient-to-detector distance or sample-to-detector distance does not create unacceptable geometric blur given the divergence of the finite x-ray source. A scatter rejection device preferentially transmits the primary beam (the beam passing through the object in a straight line from the source) and removes scattered beams, or a scatter rejection device may be positioned to preferentially transmit coherently-scattered radiation and to remove non-coherently scattered radiation. One example of a scatter rejection device is the grid illustrated in FIG. 3. The grid may comprise thin ribbons of a highly absorbing material such as lead interspersed with a low Z interspacing material such as carbon fiber. Alternative scatter rejection devices such as soller slits or polycapillary optic angular filters may also be employed.

In the embodiments illustrated in FIGS. 7A, 7B, and 8, the detector may be film or a CCD that produces an image. Also, either film or a CCD is may be used with a phosphor to convert x rays to visible light for dose sensitive applications such as medical imaging. Alternatively, a restimuable phosphor system such as a computed radiography plate (also known as an image plate) may be employed. Direct detectors, which do not require phosphors, such as amorphous selenium detectors, may also be used.

In one embodiment of a system for the detection of the coherent scatter from a material, one or more scatter-rejection grids and x-ray detectors are placed at an angle relative to the primary beam as shown in FIG. 7A. The angular position of the one or more grids is determined from the characteristic angle of the material. Coherent scatter forms a cone emanating from each point of the sample or object to be analyzed, with the cone angle being equal to twice the Bragg angle for the material of interest. The Bragg angle depends on the structural details of the material, such as nearest neighbor spacings, and is thus sensitive to structural differences between materials with similar compositions.

Another example of grid and detector positioning in a system for detecting a material in an object that utilizes the detection of coherent scatter is illustrated in FIG. 8. In this embodiment, the system includes a grid and detector for the primary beam in addition to one or more additional grids and detectors placed at a characteristic angle of the material relative to the primary beam. One instance of a system in accordance with this embodiment may be constructed by retrofitting a conventional radiography system to include one or more scatter rejection grids at a characteristic angle of a material of interest.

A determination of grid location and grid design is facilitated by the equations in the analysis below. Also, the location of grids may be optimized for object or sample thickness. Other factors that affect the location of grids include the Bragg angle for coherent scatter for the structure of the material of interest in the object to be analyzed and the focal length of the grid.

The presence or absence of a particular material or structure may be determined with the use of a simple single-pixel detector, which monitors the radiation intensity passing through the grid. This detector may comprise, for example, an inexpensive pin diode, a phototransistor, or geiger tube, or this detector may comprise an energy-sensitive detector such as a semiconducting detector. An energy-sensitive detector may be used to increase signal-to-noise ratio by restricting the detected photons to those coherently scattered from a characteristic line of the x-ray source.

In an exemplary embodiment, the system may be used to distinguish tissue types in medical imaging. For example, breast carcinoma is known to have a peak coherent scattering angle at 1.6 nm$^{-1}$ (13°) for Mo K$\alpha$ radiation whereas fatty tissue peaks around 1.1 nm$^{-1}$ (9°). Since the peak widths of the coherent scatter from breast carcinoma and fatty tissue are about 1°, establishing whether a particular region of the breast is scattering at 9° or 13° provides an aid for diagnosis. Generally, it is advantageous if the expected signal for coherently scattered radiation has higher intensity than the background of incoherently scattered radiation. Use of nearly monochromatic radiation, grids with high grid ratios, and energy-sensitive detectors all tend to reduce incoherently-scattered background radiation.

Employing imaging detectors such as those described above facilitates the generation of a spatially resolved two-dimensional map of structure or tissue type in the object or patient. The use of strip detectors that provide both spatial resolution and energy sensitivity improves the signal-to-noise ratio of the system and, therefore, the sensitivity of the system.

In a system having a detector for radiation transmitted by the object to be analyzed, for example the embodiment illustrated in FIG. 8, the use of two or more additional grids and detector assemblies for detecting coherently-scattered radiation advantageously increases the fraction of the coherent scatter cone collected. Also, the use of back projection in a system with a detector for transmitted radiation and two or more detectors positioned to detect coherently-scattered radiation facilitates computation of three-dimensional information such as the probable depth of a suspicious region in the object to be analyzed.

Because the method and system of the present invention does not require a highly collimated input beam of radiation, a system in accordance with the present invention may concurrently sample the entire slot area of an object, i.e. a wide-field area illuminated by a source of x-ray radiation. Advantageously, this facilitates more rapid analysis of an object than a system that scans an object with a highly collimated beam. Moreover, the present invention is compatible with standard imaging such as mammographic screening. Therefore, one embodiment of a system in accordance with the present invention may be constructed by retrofitting an existing radiographic system with an additional grid and detector.

Advantageous grid location and grid parameters may be determined from modeling the intensity of the transmitted rays with reference again to FIG. 6. The first step is setting up the incident and scattered ray vectors. In the following equations, $\vec{v}_o$ is the vector from the x-ray source to the patient point $$\vec{r} = \begin{bmatrix} x \\ y \\ z \end{bmatrix}, \vec{v}_{\perp 1}$$

is perpendicular to $\vec{v}_o$, and $\vec{v}_{\perp 2}$ is perpendicular to both $\vec{v}_{\perp 1}$ and $\vec{v}_o$.

$$\vec{v}_o = \frac{1}{\sqrt{x^2 + y^2 + z^2}} \begin{bmatrix} x \\ y \\ z \end{bmatrix}, \quad \vec{v}_{\perp 1} = \frac{1}{\sqrt{y^2 + z^2}} \begin{bmatrix} 0 \\ -z \\ y \end{bmatrix} \text{ and}$$

$$\vec{v}_{\perp 2} = \frac{1}{\sqrt{x^2 y^2 + x^2 z^2 + (y^2 + z^2)^2}} \begin{bmatrix} y^2 + z^2 \\ -xy \\ -xz \end{bmatrix}.$$

Then, as in the equation below, the ray $\vec{v}_s$ scattered from an incident ray $\vec{v}_o$ emerges at an angle $2\theta_s$, with an azimuthal angle of $\phi$. This describes a cone of scattered radiation for each incident ray.

$$\vec{v}_s = \cos(2\theta_s)\vec{v}_o + \sin(2\theta_s)(\vec{v}_{\perp 1}\cos(\phi) + \vec{v}_{\perp 2}\sin(\phi))$$

The grid focal point is chosen as the intersection of two rays at an angle $2\theta_{grid}$ from the incident rays: one through the point $(0,0,z_o+d)$, and one through the point $(0,w,z_o+d)$. In the equation below, $\overrightarrow{focus}$ is the intersection point, $z_o$ is the distance from the source at $(0,0,0)$ to the patient, and $d$ is a depth into the patient. In practice, the optimal placement of the grid may occur with d negative or w outside of the actual patient or objection.

$$\overrightarrow{focus} = \begin{bmatrix} 0 \\ w\sin^2(2\theta_{grid}) + (z_o+d)\cos(2\theta_{grid})\sin(2\theta_{grid}) \\ (z_o+d)\sin^2(2\theta_{grid}) - w\cos(2\theta_{grid})\sin(2\theta_{grid}) \end{bmatrix}$$

The equation below gives the distance, D, from the patient point $(0,0,z_o+d)$ to the grid focus.

$$D = |w\sin(2\theta_{grid}) + (z_o+d)\cos(2\theta_{grid})|.$$

The equation below gives the direction of the grid normal $\vec{g}_n$, the direction that the centerline of the grid is pointing.

$$\vec{g}_n = \begin{bmatrix} 0 \\ -\sin(2\theta_{grid}) \\ \cos(2\theta_{grid}) \end{bmatrix}.$$

The center of the grid face is then the found as a distance, G, from the grid focus $\overrightarrow{focus}$ along the direction $\vec{g}_n$. The grid center location is written as $\overrightarrow{GC}$ in the equation below. In practice the optimal grid position may occur using a value of G which is either larger or smaller than the physical grid focal length, F.

$$\overrightarrow{GC} = \begin{bmatrix} 0 \\ -(G-D)\sin(2\theta_{grid}) \\ (z_o+d) + (G-D)\cos(2\theta_{grid}) \end{bmatrix}.$$

The grid face is then parameterized by GF, $$\overrightarrow{GF} = \overrightarrow{GC} + \eta \begin{bmatrix} 0 \\ \cos(2\theta_{grid}) \\ \sin(2\theta_{grid}) \end{bmatrix} + \chi \begin{bmatrix} 1 \\ 0 \\ 0 \end{bmatrix}.$$

Then the equation below gives the intersection point P of a ray scattered from a patient point $\vec{r}$ at a scattering angle $2\theta_s$ and the grid face.

$$\vec{P} = \vec{r} + \xi \vec{v}_s.$$

Solving for $\vec{P} = \overrightarrow{GF}$ gives $$\xi = \frac{D - G - (z_o+d)\cos(2\theta_{grid}) + z\cos(2\theta_{grid}) - y\sin(2\theta_{grid})}{v_{sy}\sin(2\theta_{grid}) - v_{sz}\cos(2\theta_{grid})},$$

where $v_{sy} = \vec{v}_s \cdot \begin{bmatrix} 0 \\ 1 \\ 0 \end{bmatrix}$ and $v_{sz} = \vec{v}_s \cdot \begin{bmatrix} 0 \\ 0 \\ 1 \end{bmatrix}$.

An ideal crossed grid would then have its lead ribbons at the point of impact pointing in the direction $\vec{g}$, given in the equation below.

$$\vec{g} = \frac{\vec{P} - \overrightarrow{focus}}{|\vec{P} - \overrightarrow{focus}|}.$$

A conventional linear grid thus has ribbons with the normal vector $\vec{m}$ given the equation below.

$$\vec{m} = \frac{1}{\sqrt{g_y^2 + g_z^2}} \begin{bmatrix} 0 \\ g_z \\ -g_y \end{bmatrix}, \text{ where } g_y = \vec{g} \cdot \begin{bmatrix} 0 \\ 1 \\ 0 \end{bmatrix} \text{ and } g_z = \vec{g} \cdot \begin{bmatrix} 0 \\ 0 \\ 1 \end{bmatrix}.$$

The angle at which the ray hits the lead ribbon, $\alpha$, is then $$\alpha = \left| \frac{\pi}{2} - a\cos(\vec{m} \cdot \vec{v}_s) \right|.$$

Figure 9:
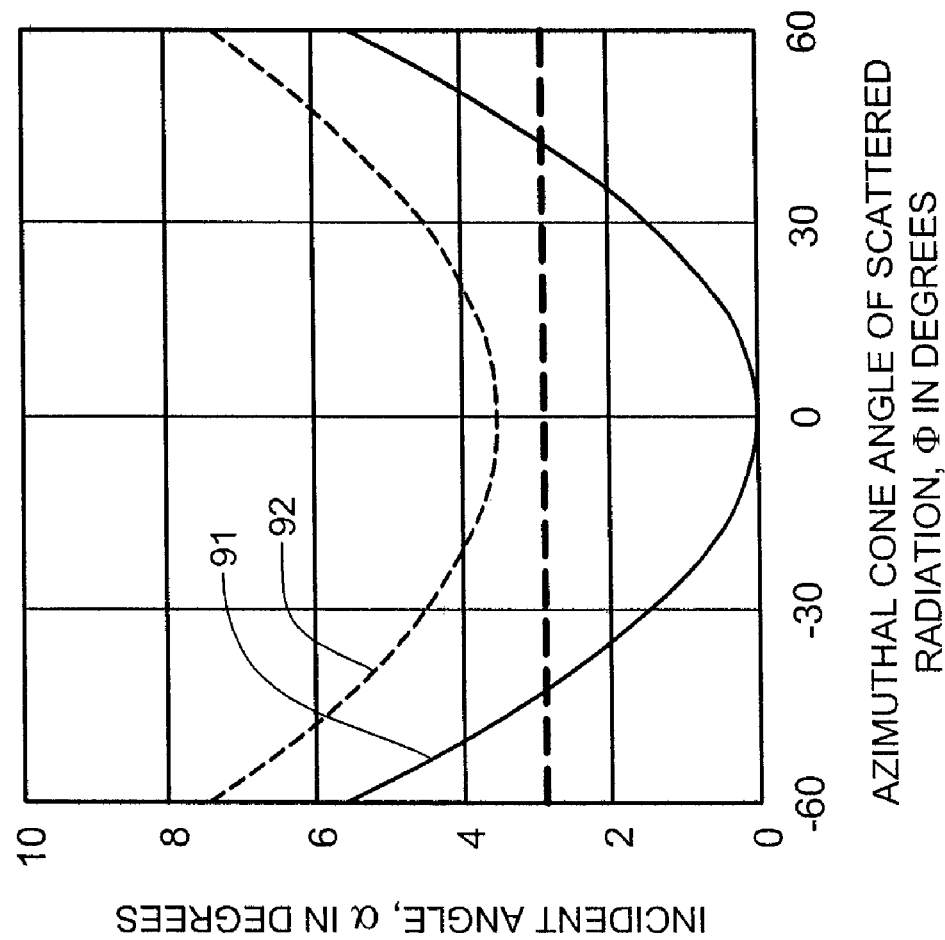
FIG. 9 illustrates plots for the incident angle to a grid of a scattered ray as a function of out-of-plane angle $\phi$ for rays scattered by cancerous tissue and rays scattered by fat.

The angle $\alpha$ is plotted versus the azimuthal angle $\phi$ of the scattered ray for the example of a grid aligned to a $2\theta$ angle of 15° in FIG. 9. Plot 91 represents the incident angles for cancerous tissue, and plot 92 represents the incident angles for fatty tissue.

The ray is then transmitted through the grid with a probability dependent on the grid resolution $\epsilon$, $$\varepsilon = a\tan\left(\frac{1}{2 \cdot \rho_{ts}}\right),$$

where $\rho_{ts}$ is the grid thickness divided by the grid spacing. Most of the incident rays pass through the grid if the angle of incidence, $\alpha$, is near zero. Approximately half the rays pass through the grid if the angle of incidence, $\alpha$, is equal to $\epsilon$. As seen in FIG. 9, the condition that the incident angle is less than a particular grid resolution is satisfied for some range of azimuthal angles, i.e. some part of the scattered radiation cone, if the grid angle $2\theta_{grid}$ is chosen to be close to the scattering angle $2\theta_s$. A larger range of azimuthal angles for which $\alpha < \epsilon$ gives a larger intensity fraction transmitted through the grid. This provides discrimination based on tissue types with differing $2\theta_s$. Assigning probabilities of transmission to incident angles $\alpha$ yields a plot of transmission versus azimuthal cone angle such as shown in FIG. 4. Averaging the transmission over azimuthal angle gives the net intensity fraction transmitted through the grid, so that a single pixel detector placed behind the grid could be used to signal the presence of a particular material or tissue type.

Combining the transmission of the scattered ray with the location of the intersection point P on the grid face yields a plot of the expected image if an area detector is employed, as shown in FIG. 5. The intensity at the overlap points is higher than at the tails, so the resulting measured images are crisper than is illustrated.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A method of detecting a material in an object to be analyzed in a radiographic imaging system comprising:
   providing two-dimensional area illumination of an object with monochromatic x-ray radiation from a divergent source without restrictively collimating the x-ray radiation, said two-dimensional area illumination being wider than a pixel in two dimensions;
   rejecting the x-ray radiation scattered by the object outside of a first predetermined range of angles defined about a first characteristic angle of a first material of the object, the first characteristic angle of the first material being a first scattering angle about which the first material of the object coherently scatters the x-ray radiation; and
   detecting coherently-scattered radiation, the coherently-scattered radiation comprising the x-ray radiation diffracted by the object within the first predetermined range of angles defined about the first characteristic angle of the first material.

2. The method of claim 1 further comprising:
   rejecting the x-ray radiation scattered by the object at angles greater than a predetermined angle; and
   detecting transmitted radiation, the transmitted radiation comprising the x-ray radiation passing though the object and not scattered by the object at angles greater than the predetermined angle.

3. The method of claim 2 further comprising back projecting a coherent-scatter image signal onto a transmitted image signal, the coherent-scatter image signal being a function of the coherently-scattered radiation from the detected coherently-scattered radiation, and the transmitted image signal being a function of the transmitted radiation from the detected transmitted radiation.

4. The method of claim 3, wherein the coherent-scatter image signal comprises depth information.

5. The method of claim 1 wherein the rejecting blocks the x-ray radiation diffracted at a second characteristic angle by a second material of the object to be distinguished from the first material, the second characteristic angle being a second scattering angle about which the second material of the object coherently scatters the x-ray radiation.

6. The method of claim 1, wherein the rejecting comprises utilizing a scatter-rejection grid having a grid ratio of at least six to one, the grid ratio being a ratio of a width of a ribbon of the scatter-rejection grid to a spacing of adjacent ribbons of the scatter-rejection grid.

7. The method of claim 1, wherein the object comprises a breast.

8. The method of claim 7, wherein the first material comprises breast carcinoma.

9. The method of claim 8, wherein the x-ray radiation comprises Mo K$\alpha$ radiation and wherein the first characteristic angle is thirteen degrees.

10. The method of claim 1, wherein the providing two-dimensional area illumination comprises filtering emitted x-ray radiation from the divergent source to attenuate a K$\beta$ radiation component of the emitted x-ray radiation, wherein an absorption edge of the filtering is between a K$\alpha$ characteristic line and a K$\beta$ characteristic line of the emitted x-ray radiation.

11. A radiographic imaging system for detecting a material in an object to be analyzed, wherein the system comprises:
   a divergent source of monochromatic x-ray radiation, the divergent source configured to illuminate a two-dimensional area of an object with the monochromatic x-ray radiation, said illuminated area being wider than a pixel in two dimensions;
   at least one scatter-rejection means for rejecting the x-ray radiation scattered by the object outside of a predetermined range of angles defined about a first characteristic angle of a first material of the object, the first characteristic angle being a first scattering angle about which the first material of the object coherently scatters the monochromatic x-ray radiation; and
   at least one detector wherein each detector of the at least one detector is positioned to detect coherently-scattered radiation passing through a respective one of the at least one scatter-rejection means, the coherently-scattered radiation comprising the monochromatic x-ray radiation diffracted about the first characteristic angle by the first material if the first material is present in the object.

12. The radiographic imaging system of claim 11 further comprising:
   another scatter-rejection means for rejecting the x-ray radiation scattered by the object at angles greater than a predetermined angle; and
   another detector for detecting transmitted radiation, the transmitted radiation comprising the monochromatic x-ray radiation passing through the object and the another scatter-rejection means.

13. The radiographic imaging system of claim 12 further comprising a processor configured for back projecting a coherent-scatter image signal onto a transmitted image signal, the coherent-scatter image signal being a function of the coherently-scattered radiation detected by the at least one detector, and the transmitted image signal being a function of the transmitted radiation detected by the another detector.

14. The radiographic imaging system of claim 13 wherein the coherent-scatter image signal comprises depth information.

15. The radiographic imaging system of claim 11 wherein the at least one scatter-rejection means is configured to block the x-ray radiation diffracted at a second characteristic angle by a second material of the object to be distinguished from the first material, the second characteristic angle being a second scattering angle about which the second material of the object coherently scatters the monochromatic x-ray radiation.

16. The radiographic imaging system of claim 11 wherein the at least one scatter-rejection means comprises a scatter-rejection grid having a grid ratio of at least six to one, the grid ratio being a ratio of a width of a ribbon of the scatter-rejection grid to a spacing of adjacent ribbons of the scatter-rejection grid.

17. The radiographic imaging system of claim 11, wherein the object comprises a breast.

18. The radiographic imaging system of claim 17, wherein the first material comprises breast carcinoma.

19. The radiographic imaging system of claim 18, wherein the monochromatic x-ray radiation comprises Mo Kα radiation and wherein the first characteristic angle is thirteen degrees.

20. The radiographic imaging system of claim 11, wherein the divergent source comprises an x-ray tube; and a transmission filter having an absorption edge between a Kα characteristic line and a Kβ characteristic line of x-ray radiation emitted by the x-ray tube.

* * * * *